United States Patent [19]

Tamborski et al.

[11] 4,367,343

[45] Jan. 4, 1983

[54] SYNTHESIS OF TETRAALKYLSILANES

[75] Inventors: Christ Tamborski, Dayton; Carl E. Snyder, Jr., Trotwood, both of Ohio

[73] Assignee: The United States of America as represented by the Secretary of the Air Force, Washington, D.C.

[21] Appl. No.: 336,474

[22] Filed: Dec. 31, 1981

[51] Int. Cl.$^3$ ............................................... C07F 7/08
[52] U.S. Cl. ...................................... 556/478; 556/480
[58] Field of Search ................................ 556/478, 480

[56] References Cited

U.S. PATENT DOCUMENTS

| 2,129,281 | 9/1938 | Lincoln et al. | 87/9 |
|---|---|---|---|
| 2,286,763 | 6/1942 | Rochow | 556/480 |
| 2,413,582 | 12/1946 | Rust et al. | 556/478 |
| 2,626,270 | 1/1953 | Sommer | 260/448.2 |
| 2,628,246 | 2/1953 | MacKenzie et al. | 556/478 X |
| 2,872,471 | 2/1959 | Ramsden et al. | 260/448.2 |
| 2,927,004 | 3/1960 | Girardot | 556/478 X |
| 2,962,446 | 11/1960 | Cook | 252/78 |
| 3,398,171 | 8/1968 | Giraitis et al. | 556/478 |
| 4,116,993 | 9/1978 | Bluestein et al. | 556/480 X |

OTHER PUBLICATIONS

Rosenberg et al., J. Org. Chem., 25, pp. 243–246, 1960.

Primary Examiner—Paul F. Shaver
Attorney, Agent, or Firm—Donald J. Singer; Charles E. Bricker

[57] ABSTRACT

A mixture of tetraalkylsilanes is prepared by reacting a mixture of at least two organometallic compounds with a silicon tetrahalide or an alkyl silicon trihalide. The mixture of silanes is useful as a hydraulic fluid.

9 Claims, No Drawings

SYNTHESIS OF TETRAALKYLSILANES

RIGHTS OF THE GOVERNMENT

The invention described herein may be manufactured and used by or for the Government of the United States for all governmental purposes without the payment of any royalty.

BACKGROUND OF THE INVENTION

This invention relates to a process for producing tetraalkylsilanes, and in particular to a process for producing mixed alkylsilanes.

In recent years, many fluid development programs have been directed toward providing base fluids for use in a variety of high temperature aerospace applications, such as jet engine oils, greases and hydraulic fluids. In applications, such as greases and jet engine oils, where oxidative stability at elevated temperatures is essential, most attention has been directed to perfluorinated fluids and modified polyphenyl ether fluids. Hydraulic fluids are not expected to operate in oxidative environments; therefore, the main areas of concern for hydraulic fluids are thermal stability and hydrolytic stability.

For certain environments, hydraulic fluids must be stable over a wide temperature range. For several years, a highly refined deep dewaxed paraffinic mineral oil has been employed as the base stock for hydraulic fluids having a service range of $-40°$ to $+550°$ F. As operating temperature requirements become more demanding, such as a requirement for an operating temperature range of $-65°$ to $+600°$ F., other materials have been investigated as potential replacements for this mineral oil base stock, because the latter does not have adequate viscosity-temperature properties to provide a hydraulic fluid capable of meeting the viscosity requirements for a $-65°$ to $+600°$ F. hydraulic fluid.

It has been suggested that the more stringent requirements could be satisfied by synthetic hydrocarbon fluids based on hydrogenated polyalphaolefin oligomers. However, it was found that the oligomers were deficient both in viscosity-temperature properties and in thermal stability. Perfluorinated fluids have also been suggested as replacements for the mineral oil base stocks. These fluids, such as perfluoropolyalkylethers and perfluorinated alkyl ether sym-triazines, have excellent thermal and oxidative stabilities. However, the perfluorinated fluids have disadvantages, the most significant of which include high density, poor bulk modulus, elastomer incompatability, etc. Additionally, there is the disadvantage associated with designing a functional hydraulic system around a new class of fluids. Further, hydraulic fluids are complex formulations of a high quality base stock and several functional, property improving additives such as antiwear agents, antioxidants, rubber swell agents and antifoam additives. While such property improving additives are available for hydrocarbon base stocks, additives for the perfluorinated fluids are not available and must be specially synthesized.

Organosilicon fluids are widely employed as adjuncts or substitutes for hydrocarbon oil base hydraulic fluids. Lincoln et al, U.S. Pat. No. 2,129,281, disclose a lubricant comprising a major proportion of a hydrocarbon oil and a minor proportion of an organic silicon compound such as, for example, tetralauryl silane. Ramsden et al, U.S. Pat. No. 2,872,471, disclose that alkyl silanes make excellent hydraulic fluids, e.g., didecyldidodecyl silane is an excellent hydraulic fluid for uses involving wide variations in temperature. Cook, U.S. Pat. No. 2,962,446, discloses that tetraalkyl silanes, in which the alkyl groups are the same or different, are useful as hydraulic fluids.

Heretofore, the development of mixed alkyl silicon fluids has been stifled by the lack of convenient methods for their preparation. For example, preparation of a compound such as

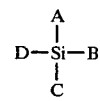

where A, B, C and D are alkyl groups, has proceeded in stepwise fashion. The first step involves the making of an alkyl metallic compound, such as an alkyllithium compound e.g. ALi:

$$ACl + 2Li \rightarrow ALi + LiCl \quad (1)$$

Step 2 involves reacting the alkyllithium compound with silicon tetrachloride:

$$ALi + SiCl_4 \rightarrow ASiCl_3 + LiCl \quad (2)$$

Subsequent steps are as follows:

$$BCl + 2Li \rightarrow BLi + LiCl \quad (3)$$

$$BLi + ASiCl_3 \rightarrow ABSiCl_2 + LiCl \quad (4)$$

$$CCl + 2Li \rightarrow CLi + LiCl \quad (5)$$

$$CLi + ABSiCl_2 \rightarrow ABSiCCl + LiCl \quad (6)$$

$$DCl + 2Li \rightarrow DLi + LiCl \quad (7)$$

$$DLi + ABSiCCl \rightarrow ABSiCD + LiCl \quad (8)$$

We have discovered a simpler process for producing mixed tetraalkylsilanes.

Accordingly, it is an object of the present invention to provide a process for producing mixed alkyl silane fluids.

Other objects and advantages of the present invention will become apparent to those skilled in the art from the following disclosure.

DESCRIPTION OF THE INVENTION

In accordance with the present invention, there is provided a process for producing a mixture of tetraalkylsilane compounds of the formula $$R_a SiR'_b R''_{4-a-b}$$

wherein a is an integer having a value ranging from 0 to 2, b is an integer having a value ranging from 0 to 4, and the sum of a plus b has a value ranging from 0 to 4, R, R' and R" are alkyl radicals containing from 1 to 20 carbon atoms, preferably 8 to 14 carbon atoms, and R, R' and R" are different, which comprises reacting a halosilicon compound of the formula $$R_a SiX_{4-a}$$

wherein R and a are as described above, and X is a halogen preferably Cl or Br, with at least two organometallic compounds having the formulas R'M and R"M wherein R and R' are as described above and M is —Li or —MgX, wherein X is as described above.

The process of this invention is more fully illustrated by the following general reactions:

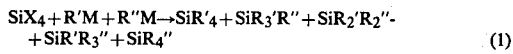

$$SiX_4 + R'M + R''M \rightarrow SiR'_4 + SiR_3'R'' + SiR_2'R_2'' + SiR'R_3'' + SiR_4'' \quad (1)$$

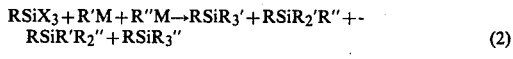

$$RSiX_3 + R'M + R''M \rightarrow RSiR_3' + RSiR_2'R'' + RSiR'R_2'' + RSiR_3'' \quad (2)$$

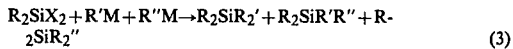

$$R_2SiX_2 + R'M + R''M \rightarrow R_2SiR_2' + R_2SiR'R'' + R_2SiR_2'' \quad (3)$$

If, instead, a mixture of three or more organometallic compounds is utilized, the number of possible products is increased.

More particularly, the invention comprises reacting at least two alkyl halides with magnesium or lithium in a suitable solvent under anhydrous conditions to form alkylmagnesium halides or alkyllithium compounds, respectively. The reaction with magnesium may require initiation, e.g., the addition of a small amount of ethyl bromide, the addition of a small amount of ethyl bromide and an iodine crystal, etc. Once the reaction has been started by the addition of a small amount of a mixture of the alkyl halides and the solvent to magnesium turnings, with initiation if necessary, it is continued by the gradual addition of the remainder of the alkyl halides-solvent mixture. The reaction is usually exothermic and it usually maintains itself under reflux conditions without the applications of external heat. After the addition is completed, the entire reaction mixture is maintained at reflux, with application of external heat, if necessary. The reaction mixture is stirred during the entire course of the process. The reaction is carried out in an inert atmosphere, such as under nitrogen or argon. When the reaction has proceeded to the point where substantially all of the alkyl halides have been converted to the alkylmagnesium halides, the reaction mixture may be filtered, in an inert atmosphere, to remove any excess magnesium.

The reaction with lithium is carried out in similar fashion, except that initiation of the reaction is generally not required and the application of external heat to complete the reaction is generally not required.

The mixture of alkylmagnesium halides or alkyllithium compounds is then reacted with the silicon reactant by adding a solution or physical mixture of the reactant in a suitable solvent to the mixture of alkylmagnesium halides or alkyllithium compounds, or vice versa. The addition is made gradually, with stirring and under an inert atmosphere. The reaction mixture is then heated to or near reflux and so maintained until reaction has proceeded to the desired degree of completion.

Separation is effected by hydrolyzing the reaction mixture to obtain the water soluble products, such as the magnesium halide or lithium halide, in the aqueous phase, and the tetraalkylsilanes in the hydrocarbon phase. The hydrocarbon phase is then separated, dried, and the solvent is removed by distillation.

The product of the present process is a mixture of tetraalkylsilanes. For example, the reaction of methyl trichlorosilane with a mixture of octylmagnesium bromide and decylmagnesium bromide yields a mixture of methyl trioctyl silane, methyldecyldioctylsilane, methyloctyldidecylsilane, methyltridecylsilane. Another example is the reaction of methyltrichlorosilane with a mixture of octyllithium and nonyllithium which yields a mixture of methyltrioctysilane, methyldioctylnonylsilane, methyloctyldinonylsilane, and methyltrinonylsilane.

The product mixture obtained by the process of this invention may be separated into individual components by conventional methods. However, the product mixture may be employed directly as the base for a hydraulic fluid or lubricant, or as a heat transfer media. The distribution of the various products in the reaction mixture is controlled by the stoichiometry of the reactants. For example, in the reaction of $RSiX_3$ with a 1:1 molar mixture of R'M and R''M, the product distribution is about 14% $RSiR_3'$, 40% $RSiR_2'R''$, 37% $RSiR'R_2''$ and 9% $RSiR_3''$. As another example, in the reaction of $RSiX_3$ with a 70:30 (molar) mixture of R'M and R''M, the product distribution is about 28% $RSiR_3'$, 48% $RSiR_2'R''$, 22% $RSiR'R_2''$ and 2% $RSiR_3''$. In general the molar ratio of R'M to R''M can range from about 10:1 to about 1:10. To ensure complete reaction, it is preferred to employ about 10 percent excess of the R'M+R''M mixture.

The solvent employed in the process of this invention may be an alkyl ether such as diethyl ether, or a simple 5 or 6 member heterocyclic compound containing one oxygen in the ring so long as the solvent is not reactive with any of the reactants or products. Typical heterocyclic compounds include tetrahydrofuran, tetrahydropyran, 2-methyltetrahydrofuran, dihydropyran, tetrahydrofurfuryl ether and the like.

The process conditions for the process of this invention will vary according to the particular tetraalkyl silanes being prepared and the organometallic reactant being employed. The tetraalkyl silanes containing the longer chain alkyl groups are the more difficult to prepare and require the use of a higher boiling solvent and/or a longer reaction time. The shorter chain alkyl silanes may be prepared in lower boiling solvents. In general the reaction temperature depending on the boiling point of the solvent will be in the approximate range of 20° to 125° C. and the reaction time will be in the approximate range of 30 minutes to 40 hours. The following examples illustrate the invention.

EXAMPLE I

Preparation of $n$-$C_8H_{17}Li$ + $n$-$C_9H_{19}Li$ Mixture

Into a two-liter, 4-necked round bottom flask equipped with a stirrer, low temperature thermometer, and a dropping funnel, and kept under an atmosphere of dry nitrogen gas, was placed 600 ml of anhydrous diethyl ether. 9.31 g (1.35 mole) of lithium ribbon, rinsed with dry hexane followed by diethyl ether, was cut into pieces about 5 mm in length which fell directly into the reaction flask through a stream of dry nitrogen. A mixture of 52.1 g (0.27 mole) of $n$-$C_8H_{17}Br$ and 55.9 g (0.27 mole) of $n$-$C_9H_{19}Br$ in 100 ml of anhydrous diethyl ether was added to the dropping funnel.

Approximately 10 ml of the mixed alkyl bromide solution was added from the dropping funnel. The reaction mixture was stirred at room temperature until the reaction started as evidenced by the lithium particles assuming a bright shiny appearance. The mixture was then cooled to approximately −10° C. with a dry ice-acetone bath. The remainder of the mixed alkyl bromide solution was added dropwise over a period of about 1.5 hours while maintaining the temperature at about −10° C. After all the halide mixture was added and stirred for an additional 30 minutes at −10° C., the reaction mixture was allowed to warm up to about +10° C. and stirred for an additional hour. A sample was withdrawn, hydrolyzed with dilute HCl and the ether layer analyzed by GC. The following products were indicated (by GC area %) n-$C_8H_{18}$ (47.2%), n-$C_9H_{20}$ (51.2%) (both from the hydrolysis of the organolithium reagents); n-$C_8H_{17}Br$ (<0.5%); plus a mixture of hydrocarbons n-$C_{16}H_{34}$, $C_{17}H_{36}$, $C_{18}H_{38}$ (<0.5%) from the coupling of the organolithium compounds with the alkylbromides.

EXAMPLE II

Preparation of $CH_3Si(n\text{-}C_8H_{17})_y(n\text{-}C_9H_{19})_{3-y}$

To the mixture of organolithium compounds prepared in Example I was added 12.0 g (0.14 mole) of methyltrichlorosilane in 20 ml of diethylether dropwise over a period of about 20 minutes at about −10° C. The reaction mixture was then stirred at room temperature for 18 hours. The reaction mixture was filtered to remove excess lithium particles and LiCl salt. The filtrate was hydrolyzed with a dilute solution of HCl in ice water. The ether layer was dried over anhydrous magnesium sulfate. The ether was then removed with a rotary evaporator. Distillation of the mixture produced a mixture of alkylsilanes having a boiling point range of 162°–185° C./0.014 mm, 94% yield. GC analysis of the mixture indicated the following composition (in GC area %): $CH_3Si(n\text{-}C_8H_{17})_3$, 14.2%; $CH_3Si(n\text{-}C_8H_{17})_2(n\text{-}C_9H_{19})$, 40.2%; $CH_3Si(n\text{-}C_8H_{17})(n\text{-}C_9H_{19})_2$, 37.2%; and $CH_3Si(n\text{-}C_9H_{19})_3$, 9.4%. Viscosity data for this mixture are given in Table I, below.

EXAMPLE III

Preparation of n-$C_8H_{17}MgBr$ and n-$C_{10}H_{21}MgBr$ Mixture

Into a one-liter, 4-necked round bottom flask equipped with a stirrer, reflux condenser, addition funnel and thermometer was added 18.0 g (0.75 mole) of Grignard grade magnesium chips. The flask was gently heated under nitrogen while the Mg chips were rapidly stirred for 1 and ½ hours, to activate the Mg. 50 ml of freshly distilled THF was added to the flask. A mixture of 81.1 g (0.47 mole) of n-octyl bromide and 39.8 g (0.18 mole) of n-decyl bromide in 600 ml of anhydrous THF was introduced into the dropping funnel. Approximately 10 ml of the mixed alkyl bromide/THF solution was added to the Mg/THF mixture in the flask. After a few minutes, the reaction started as evidenced by a rise in temperature from room temperature to about 30° C. The remainder of the mixed alkyl bromide solution was added over about 2 hours while maintaining the reaction temperature at about ∼30° C. After all the mixed halide solution was added, the reaction mixture was stirred for an additional 2 hours at about 25° C. The reaction mixture was filtered under nitrogen to remove any excess Mg. GC analysis of a hydrolyzed aliquot sample of the filtrate indicated the following products (in GC area %): n-$C_8H_{18}$, 64.9%; n-$C_{10}H_{22}$, 35.0% (both from the hydrolysis of the mixed Grignard reagents); $C_{16}H_{34}+C_{18}H_{38}+C_{20}H_{42}$, 0.10%.

EXAMPLE IV

Preparation of $CH_3Si(n\text{-}C_8H_{17})_y(n\text{-}C_{10}H_{21})_{3-y}$

To the mixture of Grignard reagents prepared in Example III was added 24.7 g (0.165 mole) of methyltrichlorosilane. The reaction mixture was refluxed for about 40 hours. The reaction mixture was poured slowly into ice water, stirred for about 10 minutes, and filtered to remove excess Mg. Dilute HCl was added to the filtrate until the mixture was slightly acidic. The organic layer was separated, dried over anhydrous magnesium sulfate, and concentrated on a rotary evaporator. The crude product was fractionally distilled to produce a mixture of alkylsilanes having a boiling point range of 142°–175° C./0.004 mm, 82% yield. GC analysis of the mixture indicated the following composition (in GC area %): $CH_3Si(n\text{-}C_8H_{17})_3$, 28.0; $CH_3Si(n\text{-}C_8H_{17})_2(n\text{-}C_{10}H_{21})$, 48.0%; $CH_3Si(n\text{-}C_8H_{17})(n\text{-}C_{10}H_{21})_2$, 21.7%; and $CH_3Si(n\text{-}C_{10}H_{21})_2$, 2.3%. Viscosity data for this mixture are given in Table I below.

EXAMPLE V

A series of runs was carried out in which mixtures of tetraalkylsilanes were prepared as described above in Examples I-IV. These tetraalkylsilane mixtures are set forth in Table I below, which indicates the relative quantity of each component of the mixture, carbon number, boiling point range, % yield, and viscosity data for each mixture.

TABLE I

| | Properties of Alkylsilanes $RSiR'_yR''_{3-y}$ | | | | | | | | |
|---|---|---|---|---|---|---|---|---|---|
| | | Carbon | | % | Viscosity, Centistokes | | | | |
| Example | | No. | BP/MM °C. | Yield | −65° F. | −40° F. | 100° F. | 210° F. | 400° F. |
| V | R = $CH_3$; R' = n-$C_8H_{17}$; R'' = n-$C_9H_{19}$ $y_3$ (7%); $y_2$ (32%), $y_1$ (44%), $y_0$ (17%) | 25–28 | 180–182/0.06 | 91 | 2019 | — | 9.42 | 2.69 | 1.00 |
| II | R = $CH_3$; R' = n-$C_8H_{17}$; R'' = n-$C_9H_{19}$ $y_3$ (14%); $y_2$ (40%), $y_1$ (37%), $y_0$ (9%) | 25–28 | 162–185/0.014 | 94 | 2020 | 505 | 9.42 | 2.69 | — |
| V | R = $CH_3$; R' = n-$C_8H_{17}$; R'' = n-$C_{10}H_{21}$ $y_3$ (12%), $y_2$ (54%), $y_1$ (30%), $y_0$ (4%) | 25–31 | 141–177/0.01 | — | 3067 | 515 | 10.31 | 2.53 | — |
| IV | R = $CH_3$; R' = $C_8H_{17}$; R'' = n-$C_{10}H_{21}$ $y_3$ (28%), $y_2$ (48%), $y_1$ (22%), $y_0$ (2%) | 25–31 | 142–175/0.004 | 82 | 2057 | 506 | 9.65 | 2.41 | — |
| V | R = $CH_3$; R' = n-$C_9H_{19}$; R'' = n-$C_{10}H_{21}$ $y_3$ (19%), $y_2$ (43%), $y_1$ (31%), $y_0$ (7%) | 28–31 | 184 (0.008) | 55 | 6501 | — | 11.41 | 3.10 | 1.10 |
| V | R = $CH_3$; R' = n-$C_9H_{19}$; R'' = n-$C_{10}H_{21}$ | | | | | | | | |

TABLE I-continued

| Example | Properties of Alkylsilanes $RSiR'_yR''_{3-y}$ | Carbon No. | BP/MM °C. | % Yield | Viscosity, Centistokes −65° F. | −40° F. | 100° F. | 210° F. | 400° F. |
|---|---|---|---|---|---|---|---|---|---|
| V | $y_3$ (9%), $y_2$ (36%), $y_1$ (42%), $y_0$ (13%) $R' = CH_3$; $R' = n-C_9H_{19}$; $R'' = n-C_{10}H_{21}$ | 28–31 | 184–200/0.008 | 80.0 | 3501 | — | 12.45 | 3.22 | 1.10 |
|  | $y_3$ (17%), $y_2$ (31%), $y_1$ (32%), $y_0$ (20%) | 28–31 | 184–200/0.008 | — | 3226 | — | 11.96 | 3.19 | 1.10 |

EXAMPLE VI

Formulation and Testing of Hydraulic Fluid

The mixture of alkylsilanes prepared in Example V and designated $CH_3Si(n-C_8H_{17})_y(n-C_9H_{19})_{3-y}$ wherein $y_3=7\%$, $y_2=32\%$, $y_1=44\%$ and $y_0=17\%$, was tested for thermal stability, then formulated and tested with additives typically used in hydraulic fluids.

Initial thermal stability determinations were conducted on a microscale using a stainless steel test bomb. The bomb used was 0.625 cm O.D. by 22.5 cm, type 304 stainless steel tube, capped with a type 316 stainless steel cap fitting. The bomb was flushed with nitrogen then charged with 2 ml of the sample. After sealing, the bomb was heated at 371° C. (700° F.) for 6 hours, after which fluid stability was determined by comparing gas chromatographic analyses and 38° C. (100° F.) viscosities of the samples before and after heating. The microthermal stability data are presented below in Table II.

TABLE II

| Micro Thermal Stability Test | |
|---|---|
| Viscosity change at 100° F., % | −11.6 |
| Acid No. MgKOH/g | <0.1 |
| % Change in GC | −5.3 |

The alkylsilane mixture was formulated with tricresyl phosphate (TCP), which is commonly used as a lubricity additive in hydrocarbon base hydraulic fluids, and dibutyl chlorendate (DBC), which has been used as a lubricity additive in silicon hydrocarbon fluids, and the various formulations were subjected to the four-ball wear scar test using a 40 Kg load at 600 rpm and 75° C. (167° F.) for 1 hour. The TCP formulations additionally contained 1% of 2,6-di-t-butyl phenol as an oxidation inhibitor. The test results are given in Table III below.

TABLE III

| | Four-Ball Wear Data | |
|---|---|---|
| Additive | Concentration, % | Wear Scar (mm) |
| none | — | 0.94 |
| TCP | 0.5 | 0.81 |
| TCP | 1.0 | 0.93 |
| TCP | 3.0 | 0.62 |
| TCP | 5.0 | 0.53 |
| DBC | 1.0 | 0.75 |

TABLE III-continued

| | Four-Ball Wear Data | |
|---|---|---|
| Additive | Concentration, % | Wear Scar (mm) |
| DBC | 4.0 | 0.58 |

It can be seen that a minimum of about 3% TCP or 4% DBC is necessary to bring about any significant reduction in the average four-ball wear scar.

Formulations were prepared containing 3% TCP and 0.5 and 1.0% 2,6-di-t-butyl phenol. These formulations were tested for oxidation-corrosion stability at 347° F. for 48 hours under a 5 l/hr air flow in a reflux configuration according to MIL-H-27601. The test results are presented in Table IV below.

TABLE IV

| Oxidation-Corrosion Stability | | | | | | | | |
|---|---|---|---|---|---|---|---|---|
| Oxidation Inhibitor, % | TCP, % | Viscosity Change at 100° F. % | Acid No. Change MgKOH/g | Metal Weight Change (Mg/cm²) | | | | |
| | | | | Ti | 350 | 450 | Cu | Ag |
| 0.5 | 3.0 | +48.5 | 3.09 | −0.01 | +0.01 | 0.00 | −0.46 | −0.06 |
| 1.0 | 3.0 | +2.56 | 0.44 | −0.02 | −0.02 | −0.02 | −0.04 | −0.04 |

It can be seen that the formulation containing 1.0%, 2,6-di-t-butyl phenol and 3.0% TCP is the more effective of the two formulations. This composition was characterized for its thermal stability at 600° F. and at 700° F. The data are set forth in Table V, below. For comparison, data for thermal stability of the base fluid, without additives, at 700° F. is also presented.

TABLE V

| | Thermal Stability | | | | |
|---|---|---|---|---|---|
| | Viscosity Change at 100° F., % | Acid No. Change MgKOH/g | Metal Weight Change (Mg/cm²) | | |
| | | | 52100 | Navel Bronze | M-10 |
| Without Additives at 700° F. | −11.6 | <0.1 | 0.00 | −0.04 | 0.00 |
| With Additives at 600° F. | +0.3 | 0.02 | 0.02 | 0.16 | 0.04 |
| With Additives at 700° F. | −11.74 | 0.35 | 0.11 | 0.56 | 0.04 |

Although the thermal stability of the formulations is not quite as good as that of the base fluid, its thermal stability is excellent except for a relatively high degree of reactivity with the naval bronze alloy.

The present invention provides an efficient and flexible process for preparing a wide variety of alkylsilicon compounds. The alkylsilanes are characterized by extreme resistance, inertness, stability and fluidity over a wide temperature range. Thus, these materials make excellent lubricants and hydraulic fluids.

The present invention is not limited to the specific embodiments described herein.

We claim:

1. A process for producing a mixture of tetraalkylsilane compounds of the formula $$R_aSiR'_bR''_{4-a-b}$$

wherein a has a value ranging from 0 to 2, b has a value ranging from 0 to 4 and the sum of a plus b has a value ranging from 0 to 4; R, R' and R'' are alkyl radicals containing from 1 to 20 carbon atoms, and R, R' and R'' are different, which comprises reacting a halosilicon compound of the formula $$R_aSiX_{4-a}$$

wherein R and a are as described above, and X is a halogen, with at least two organometallic compounds having the formulas R'M and R''M wherein R' and R'' are as described above and M is —Li or —MgX, wherein X is as described above, for a time sufficient to convert substantially all of said halosilicon compounds to the product.

2. The process of claim 1 wherein said R is —CH$_3$ and said a is 1.

3. The process of claim 2 wherein said R' is n-C$_8$H$_{17}$ and said R'' is n-C$_9$H$_{19}$.

4. The process of claim 2 wherein said R' is n-C$_8$H$_{17}$ and said R'' is n-C$_{10}$H$_{21}$.

5. The process of claim 2 wherein said R' is n-C$_9$H$_{19}$ and said R'' is n-C$_{10}$H$_{21}$.

6. The process of claim 1 wherein the molar ratio of said R'M to said R''M in said mixture is in the approximate range of 10:1 to 1:10.

7. The process of claim 3 wherein the molar ratio of said R'M to said R''M is about 1:1.

8. The process of claim 4 wherein the molar ratio of said R'M to said R''M is about 7:3.

9. The process of claim 1 wherein said R, R' and R'' have from 8 to 14 carbon atoms per group.

* * * * *